(12) United States Patent
Baril

(10) Patent No.: US 11,786,248 B2
(45) Date of Patent: Oct. 17, 2023

(54) SURGICAL STAPLING DEVICE INCLUDING A BUTTRESS RETENTION ASSEMBLY

(71) Applicant: Covidien LP, Mansfield, MA (US)

(72) Inventor: Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 165 days.

(21) Appl. No.: 17/371,533

(22) Filed: Jul. 9, 2021

(65) Prior Publication Data
US 2023/0011980 A1    Jan. 12, 2023

(51) Int. Cl.
*A61B 17/072* (2006.01)
*A61B 17/00* (2006.01)
*A61B 17/29* (2006.01)

(52) U.S. Cl.
CPC .............. *A61B 17/07292* (2013.01); *A61B 2017/00004* (2013.01); *A61B 2017/00477* (2013.01); *A61B 2017/00862* (2013.01); *A61B 2017/07271* (2013.01); *A61B 2017/2936* (2013.01)

(58) Field of Classification Search
CPC ............ A61B 17/07292; A61B 17/105; A61B 17/1114; A61B 17/1155; A61B 17/068
See application file for complete search history.

(56) References Cited

U.S. PATENT DOCUMENTS

| | | |
|---|---|---|
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

Extended European Search Report corresponding to International Application No. EP 14 18 4882.0 dated May 12, 2015.

(Continued)

*Primary Examiner* — Nathaniel C Chukwurah
(74) *Attorney, Agent, or Firm* — Carter, DeLuca & Farrell LLP

(57) ABSTRACT

A surgical kit includes a surgical stapling device and a loading assembly. The surgical stapling device includes a tool assembly and a buttress material. The tool assembly includes first and second jaw members. The first jaw member supports a staple cartridge that includes a retention assembly. The retention assembly includes a cam block including a pair of protrusions and a spring biasing the cam block towards the second jaw member. The buttress material includes proximal and distal portions. The proximal portion defines bores laterally spaced apart and configured to receive the pair of protrusions of the cam block. The distal portion defines a cavity to be placed over a distal end portion of the staple cartridge. The loading assembly includes a housing defining a chamber configured to receive a portion of the buttress material. The housing includes a proximal portion defining a slot configured to receive the buttress material therethrough and the pair of protrusions of the cam block.

20 Claims, 14 Drawing Sheets

(56) References Cited

U.S. PATENT DOCUMENTS

| | | |
|---|---|---|
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |

(56) References Cited

U.S. PATENT DOCUMENTS

| | | | |
|---|---|---|---|
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,726,537 B2 * | 6/2010 | Olson .................. A61B 17/068 |
| | | | 227/176.1 |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,950,561 B2 * | 5/2011 | Aranyi ............. A61B 17/07207 |
| | | | 227/176.1 |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,717,498 B2 | 8/2017 | Aranyi et al. |
| 9,814,463 B2 * | 11/2017 | Williams ......... A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |

(56) References Cited

U.S. PATENT DOCUMENTS

| | | |
|---|---|---|
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0147922 A1* | 6/2010 | Olson ............... A61B 17/105 227/176.1 |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0206315 A1 | 7/2016 | Olson |
| 2018/0125491 A1 | 5/2018 | Aranyi |
| 2021/0177411 A1 | 6/2021 | Williams |

(56) References Cited

U.S. PATENT DOCUMENTS

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| JP | 2005125075 A | 5/2005 |
| KR | 20120022521 A | 3/2012 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.
International Search Report and Written Opinion dated Nov. 28, 2022, issued in corresponding international application No. PCT/IB2022/056050, 16 pages.

* cited by examiner

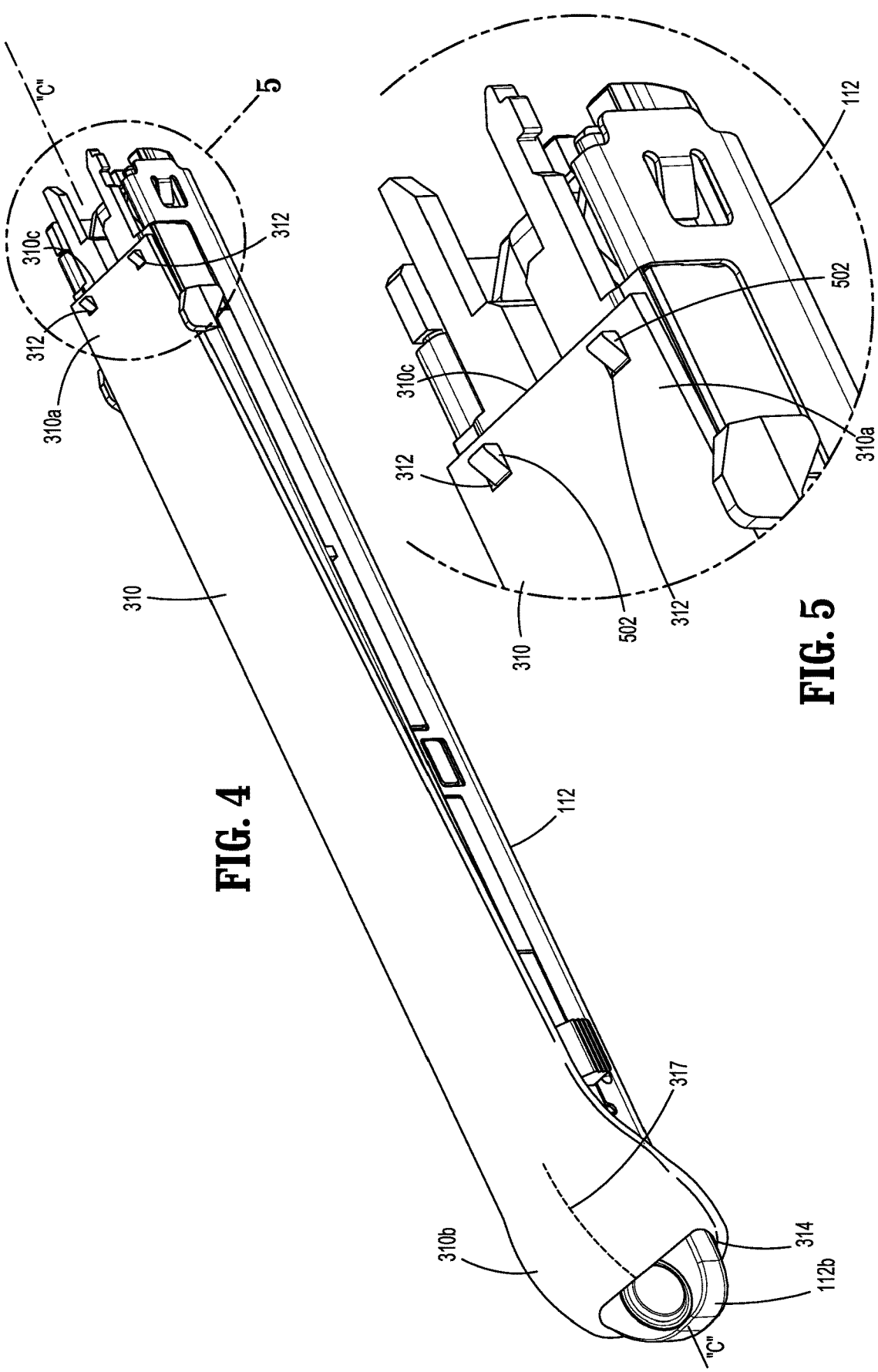

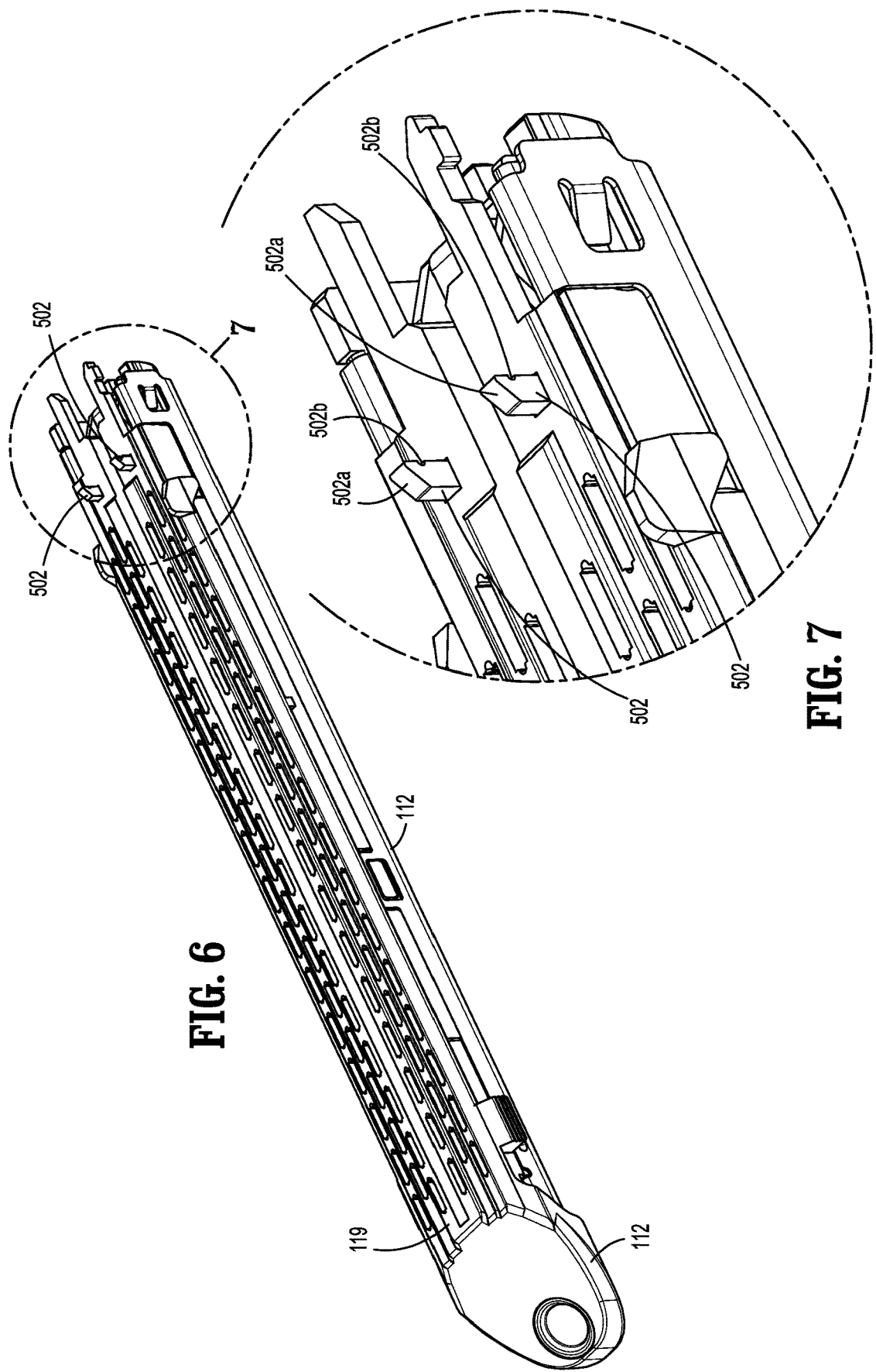

SURGICAL STAPLING DEVICE INCLUDING A BUTTRESS RETENTION ASSEMBLY

FIELD

The disclosure relates to surgical stapling devices, and more particularly, to assemblies and methods for detachably securing or retaining a staple line buttress assembly to a surgical stapling device.

BACKGROUND

Surgical stapling devices are employed by surgeons to sequentially or simultaneously apply one or more rows of fasteners, e.g., staples or two-part fasteners, to body tissue for the purpose of joining segments of body tissue together. When stapling relatively thin or fragile tissues, it is important to effectively seal the staple line against air or fluid leakage. Additionally, it is often necessary to reinforce the staple line against the tissue to inhibit tears in the tissue or pulling of the staples through the tissue. One method of inhibiting tears or pull through involves the placement of a biocompatible reinforcing material or "buttress" material between the staples and the underlying tissue. In this method, a layer of buttress assembly is placed against the tissue and the tissue is stapled in a conventional manner.

Accordingly, new systems and methods that enable easy and efficient attachment and removal of a buttress assembly to a surgical stapling device would be desirable.

SUMMARY

In accordance with the disclosure, a surgical kit includes a surgical stapling device and a loading assembly. The surgical stapling device includes a tool assembly and a buttress material. The tool assembly includes first and second jaw members that are transitionable between open and closed configurations. The first jaw member supports a staple cartridge that includes a retention assembly. The retention assembly includes a cam block including a pair of protrusions and a spring biasing the cam block towards the second jaw member. The buttress material includes proximal and distal portions. The proximal portion defines bores laterally spaced apart and configured to receive the pair of protrusions of the cam block. The distal portion defines a cavity to be placed over a distal end portion of the staple cartridge. The loading assembly includes a housing defining a chamber configured to receive a portion of the buttress material. The housing includes a proximal portion defining a slot configured to receive the buttress material therethrough and the pair of protrusions of the cam block.

In an aspect, the distal portion of the buttress material may have a weakened portion extending axially from the cavity.

In another aspect, the housing of the loading assembly may include a pair of lateral tabs on lateral sides of the housing. The staple cartridge may be positioned within the pair of lateral tabs.

In yet another aspect, the proximal portion of the housing may have a tapered surface.

In still yet another aspect, the tapered surface of the proximal portion of the housing may define an opening.

In still yet another aspect, the spring of the retention assembly may be a leaf spring.

In still yet another aspect, at least one protrusion of the pair of protrusions of the retention assembly may have a tapered portion.

In an aspect, at least one protrusion of the pair of protrusions may define a notch positioned to receive a portion of the buttress material.

In another aspect, the staple cartridge may include an inner wall defining a camming slot, and the cam block may include a camming portion configured to slidably engage the camming slot of the inner wall.

In yet another aspect, the buttress material may be formed of an elastic material and the buttress material may be in tension when secured to the staple cartridge.

In stilly yet another aspect, the pair of protrusions of the cam block may be secured to the buttress material via interference or friction fit.

In accordance with another aspect of the disclosure, a buttress assembly for use with a surgical stapling device includes a buttress material and a loading assembly. The buttress material includes proximal and distal portions. The proximal portion defines bores laterally spaced apart. The distal portion defines a cavity. The loading assembly includes a housing defining a chamber to receive a portion of the buttress material. The housing includes proximal and distal sections. The proximal section defines a slot configured to be in registration with the bores of the buttress material when the portion of the buttress material is received in the chamber of the loading assembly. The slot is dimensioned to receive the buttress material therethrough.

In an aspect, the housing may have tabs on lateral sides thereof.

In another aspect, the proximal section of the housing may have a tapered surface.

In yet another aspect, the tapered surface of the housing may have an opening.

In still yet another aspect, the buttress material may be bioabsorbable.

In still yet another aspect, the buttress material may have perforations along a central axis of the buttress material.

In still yet another aspect, the cam block may have a generally U-shaped profile.

In accordance with yet another aspect of the disclosure, a tool assembly of a surgical device includes first and second jaw members and a clamping member. The second jaw member is movable between open and closed configurations in relation to the first jaw member. The second jaw member includes a spring to bias the second jaw member towards the open configuration. The clamping member is operatively coupled to the first and second jaw members such that axial displacement of the clamping member transitions the second jaw member between the open and closed configurations.

In an aspect, the spring may be disposed laterally of the clamping member.

BRIEF DESCRIPTION OF THE DRAWINGS

The above and other aspects and features of this disclosure will become more apparent in view of the following detailed description when taken in conjunction with the accompanying drawings wherein like reference numerals identify similar or identical elements.

FIG. 4 is a perspective view of the staple cartridge of FIG. 3, illustrating a buttress material mounted on the staple cartridge;

FIG. 5 is an enlarged view of the indicated area of detail of FIG. 4;

FIG. 6 is a perspective view from above of the staple cartridge of FIG. 3, illustrating a retention assembly configured to releasably support the buttress material on the staple cartridge;

FIG. 7 is an enlarged view of the indicated area of detail of FIG. 6;

DETAILED DESCRIPTION

Figure 1:
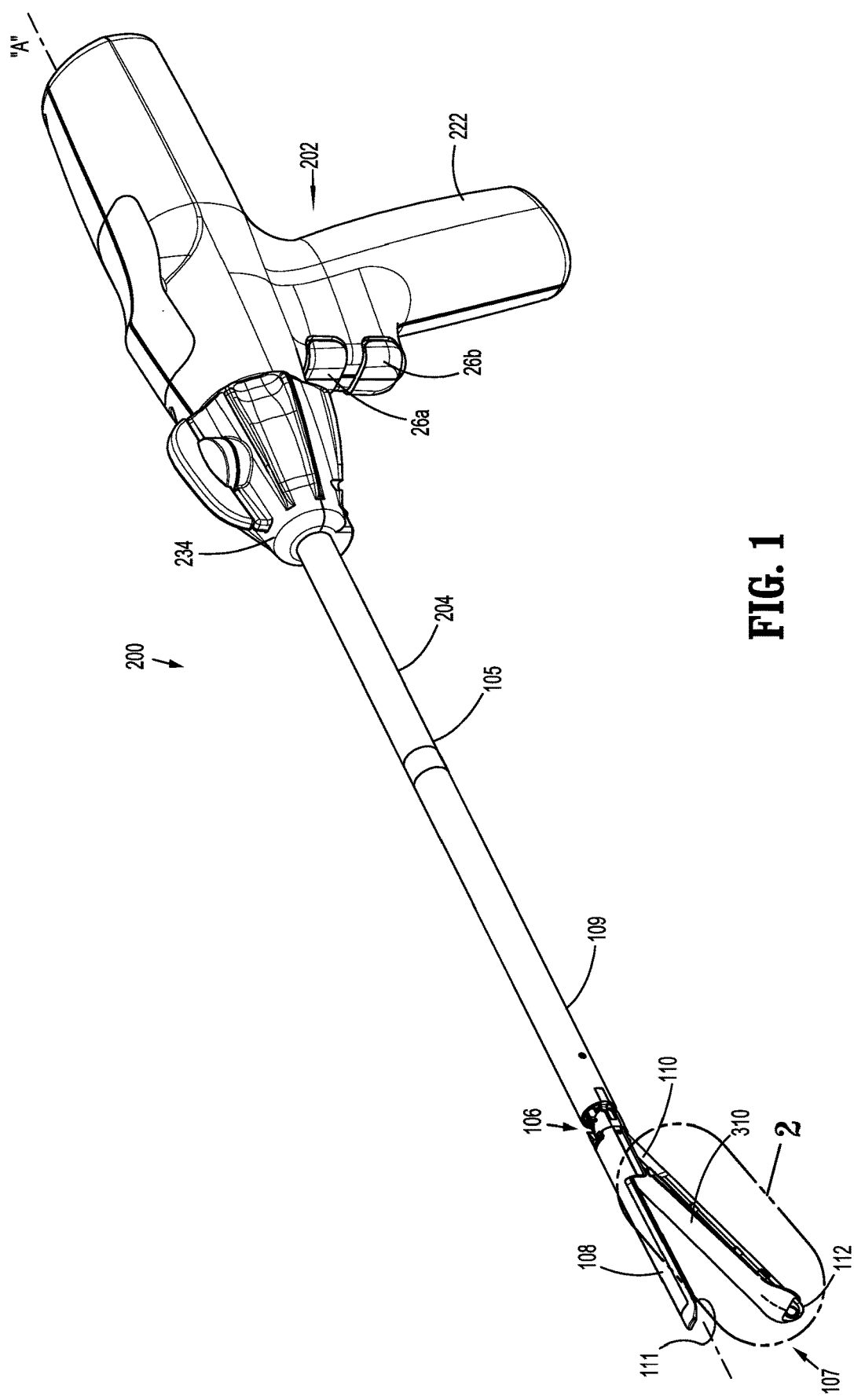
FIG. 1 is a perspective view of a surgical stapling device in accordance with the disclosure.

The surgical stapling device including a buttress retention assembly disclosed herein is described in detail with reference to the drawings, in which like reference numerals designate identical or corresponding elements in each of the several views. As used herein, the term "distal" refers to the portion of the device that is being described which is farther from a user in a conventional use of the surgical stapling device, while the term "proximal" refers to the portion of the device that is being described which is closer to a user in a conventional use of the surgical stapling device. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 2:
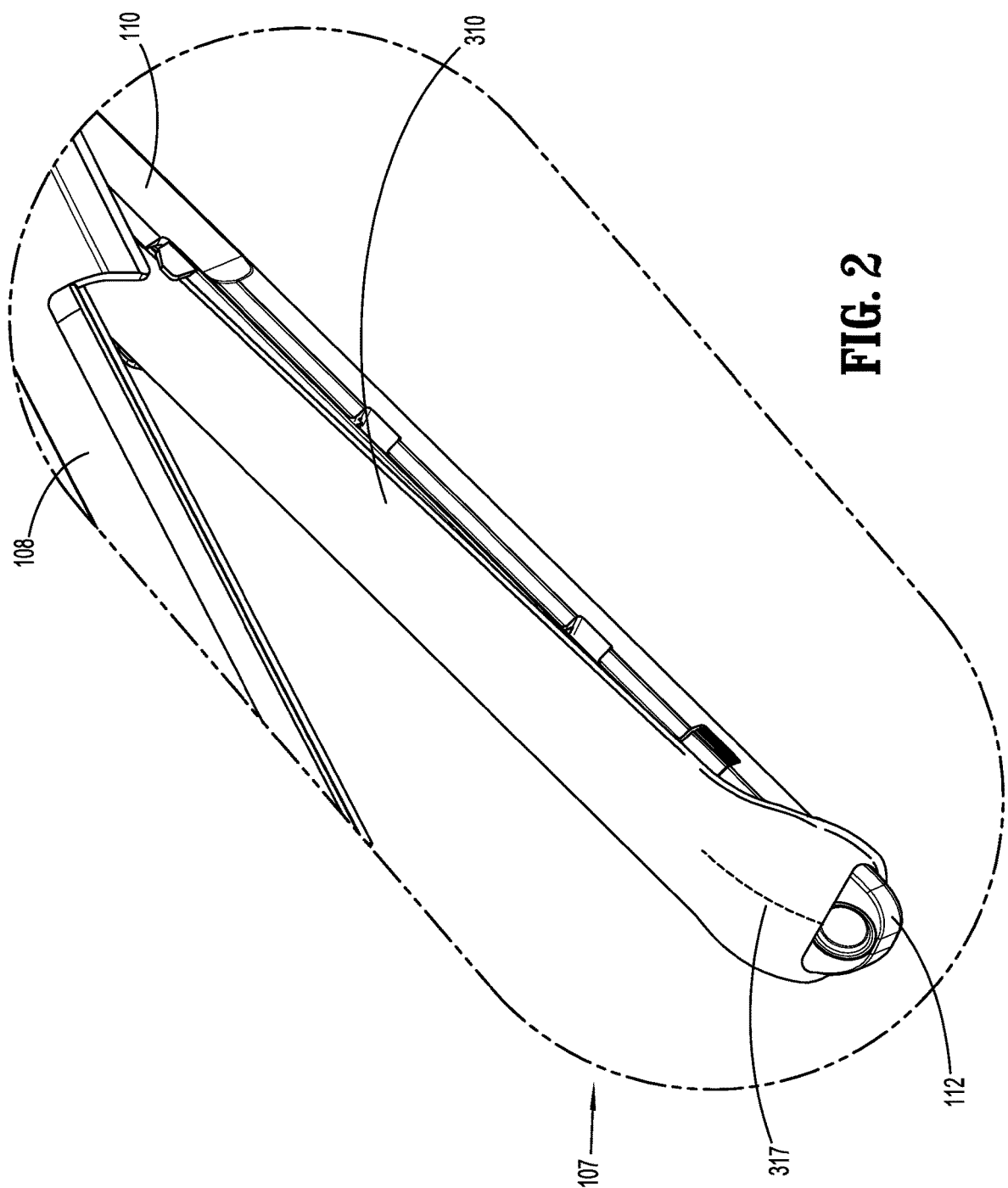
FIG. 2 is an enlarged view of the indicated area of detail of FIG. 1.

With reference to FIGS. 1 and 2, there is provided a surgical stapling device 200 for use in stapling tissue and applying a layer of buttress material 310 between staples and underlying tissue. The layer of buttress material 310 is configured to reinforce and seal staple lines applied to tissue by the surgical stapling device 200. The surgical stapling device 200 generally includes a handle 202 and an elongate tubular member 204 extending distally from the handle 202. A reload 106 is removably coupled to a distal end 105 of the elongate tubular member 204. The reload 106 includes a shaft portion 109 and a tool assembly 107 supported on the shaft portion 109. The tool assembly 107 includes first jaw member 108 and a second jaw member 110 that is movable in relation to the first jaw member 108 between an open configuration for positioning tissue between the first and second jaw members 108, 110 and a closed configuration for clamping tissue between the first and second jaw members 108, 110 and subsequently stapling tissue. The first jaw member 108 supports an anvil 111 and the second jaw member 110 releasably supports a staple cartridge 112. The buttress material 310 is mounted on the staple cartridge 112, as will be described. In order to secure the staples provided by the staple cartridge 112 to tissue and the buttress material 310, the anvil 111 is provided with longitudinally arranged rows of staple clinching or forming pockets (not shown). It is envisioned that the tool assembly 107 may be coupled to a mechanical or motorized handle, and the staple cartridge 112 may be removable and replaceable. It is also envisioned that the reload 106 may be part of a robotic surgical system.

With continued reference to FIG. 1, the surgical stapling device 200 includes a stationary grip 222 and a rotation knob assembly 234. Buttons 26a, 26b on the stationary grip 222 of the handle 202 allow for actuation of the tool assembly 107. When the button 26a is pressed, the tool assembly 107 is transitioned from the open configuration to the closed configuration and subsequently actuates the surgical stapling device 200 to apply lines of staples to tissue. When the button 26b is pressed, a firing mechanism of the surgical stapling device 200 is retracted and the tool assembly 107 is transitioned from the closed configuration to the open configuration. In order to provide proper orientation of the tool assembly 107 relative to tissue to be stapled, the surgical stapling device 200 is additionally provided with the rotation knob assembly 234 mounted on the handle 202. Rotation of the rotation knob assembly 234 about a longitudinal axis "A-A" of the surgical stapling device 200 rotates the tool assembly 107 about the longitudinal axis "A-A." The surgical stapling device 200 is illustrated as an electrically powered stapling device including the electrically powered handle 202 that may support one or more batteries (not shown). Examples of electrically powered surgical stapling devices can be found in U.S. Pat. Nos. 9,055,943 and 9,023,014. In addition, reference may be made to U.S. Pat. No. 9,717,498, the entire contents of which is incorporated herein by reference, for a detailed discussion of the construction and operation of the surgical stapling device 200.

Figure 3:
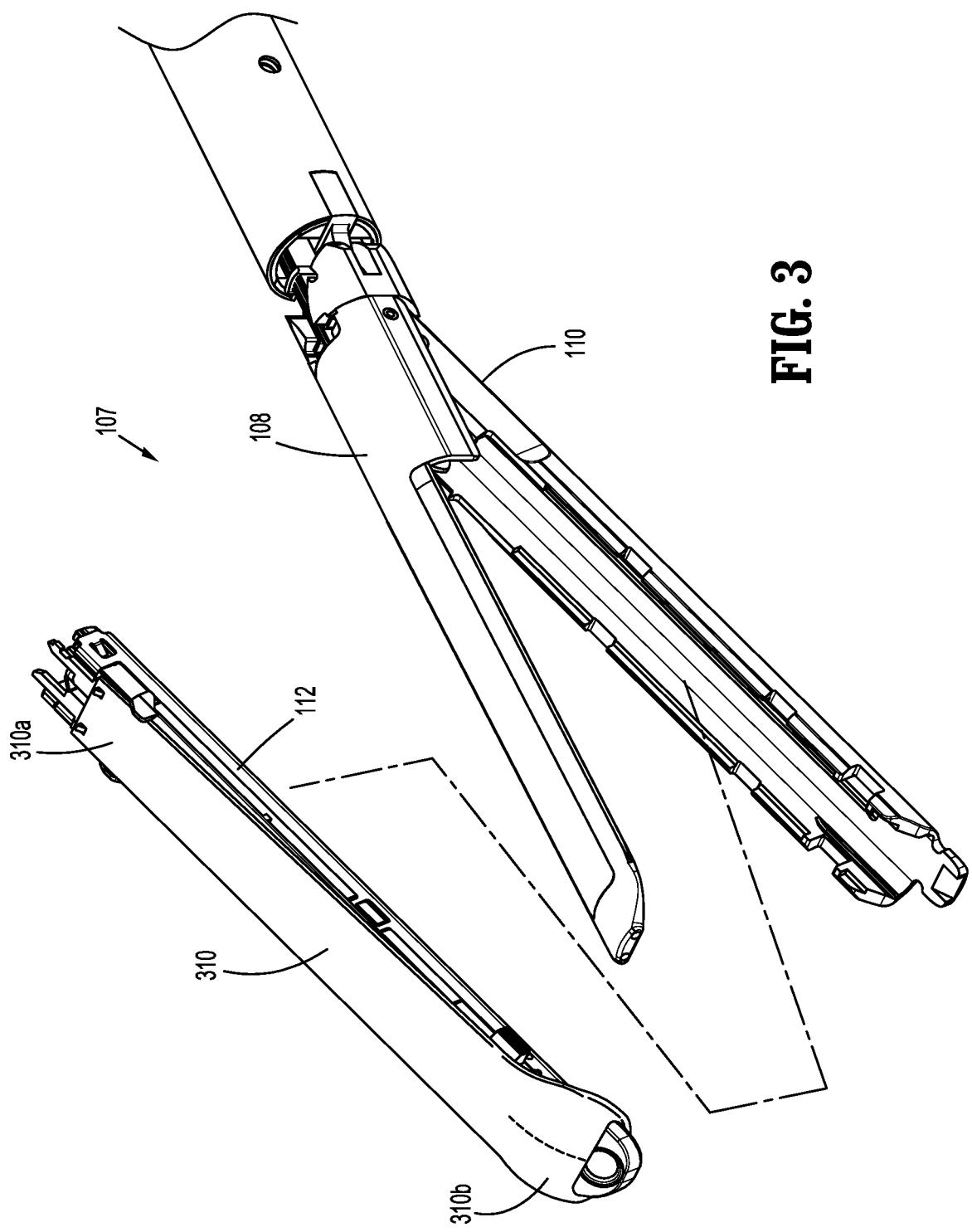
FIG. 3 is perspective view of a tool assembly of the surgical stapling device of FIG. 1, illustrating a staple cartridge separated from a jaw of the tool assembly.

FIGS. 3-5 illustrate the buttress material 310 for use with the surgical stapling device 200. The buttress material 310 is detachably secured to the tool assembly 107 of the surgical stapling device 200 to be in registration with the anvil 111 of the first jaw member 108 and the staple cartridge 112 of the second jaw member 110. The buttress material 310 is configured to reinforce and seal staple lines applied to tissue by the surgical stapling device 200. The buttress material 310 includes proximal and distal portions 310a, 310b that are detachably securable to the staple cartridge 112. In particular, the proximal portion 310a defines bores 312 that are laterally spaced apart and adjacent a proximal end 310c of the buttress material 310. The bores 312 releasably receive protrusions 502 of a cam block 500 (FIG. 8) of a retention assembly 550 of the staple cartridge 112, as will be described. The distal portion 310b of the buttress material 310 defines a cavity 314 configured to releasably receive a distal end portion 112b of the staple cartridge 112, as will be described. In an aspect, the distal end portion 112b is tapered. In another aspect, the buttress material 310 may be formed of an elastic material such that when the proximal portion 310a of the buttress material 310 is releasably secured to the cam block 500 of the retention assembly 550 of the staple cartridge 112 and the distal portion 310b of the buttress material 310 is releasably secured to the distal end portion 112b of the staple cartridge 112, the buttress material 310 is in tension to enhance securement with the staple cartridge 112. In another aspect, the buttress material 310 further includes a weakened portion 317 extending to the cavity 314 (best shown in FIG. 9). The weekend portion 317 may be centrally defined to be in alignment with a path of a knife member (not shown) of the tool assembly 107 (FIG. 1) such that the weakened portion 317 is aligned with a central axis "C-C" defined by the staple cartridge 112 or the buttress material 310. In an aspect, the weakened portion 317 may define perforations. Under such a configuration, when the knife member is advanced, the knife member cuts through the weakened portion 317 and the cavity 314 and releases the buttress material 310 from the staple cartridge 312.

Figure 8:
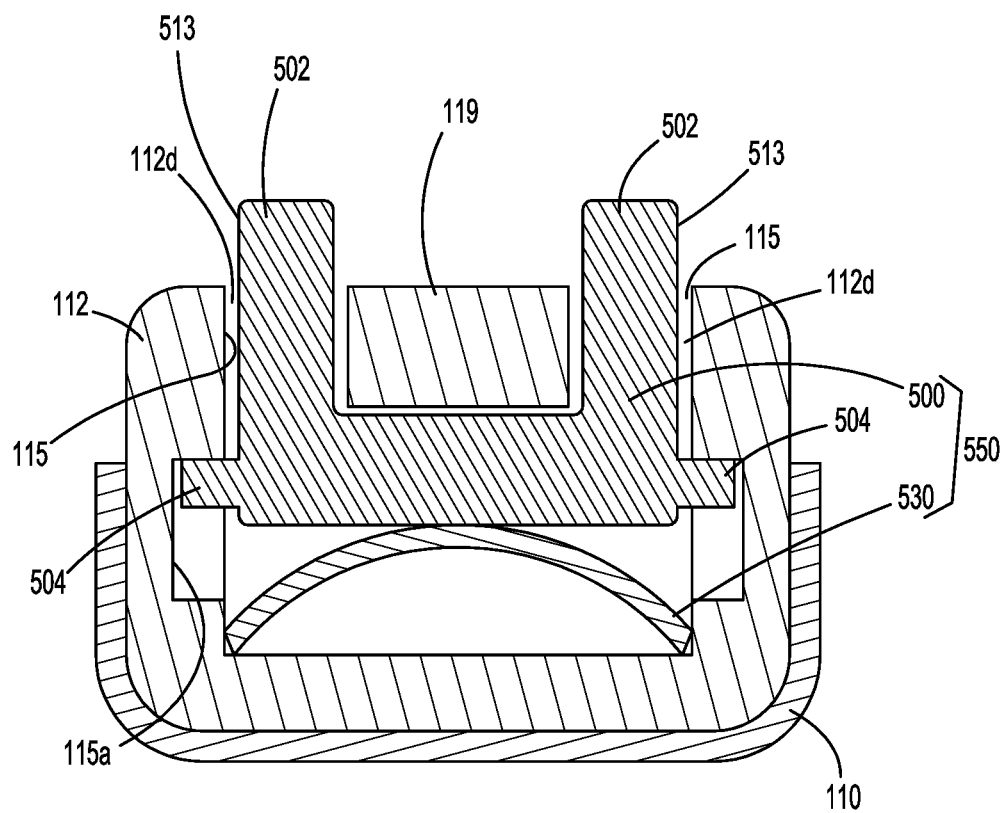
FIG. 8 is a cross-sectional view of the tool assembly of FIG. 3, illustrating the retention assembly.

The buttress material 310 is detachably securable to the tool assembly 107. To this end, the staple cartridge 112 includes the retention assembly 550 (FIG. 8) which is configured to releasably support the buttress material 310 on the staple cartridge 112. FIGS. 6-8 illustrate the retention assembly 550 which includes a cam block 550 and a spring 530 such as, e.g., a leaf spring, that biases the cam block 550 away from the second jaw member 110, i.e., towards the first jaw member 108. The cam block 500 may have a generally U-shaped profile. In an aspect, the cam block 500 is monolithically formed as a single construct and includes protrusions 502 that are laterally spaced apart. Each protrusion 502 includes a tapered portion 502a configured to facilitate sliding of a proximal portion 600a of the loading assembly 600 over the tapered portion 502a of the protrusion 502 such that the protrusions 502 are displaced into the slots 112d (FIG. 8) of the staple cartridge 112. In addition, each protrusion 502 defines a notch 502b to receive the buttress material 310, as will be described below. The spring 530 biases the cam block 500 such that the protrusions 502 of the cam block 500 extends through slots 112d defined in the staple cartridge 112. The cam block 500 further includes camming portions 504 that extend laterally outwards from lateral surfaces 513 of the cam block 500. The staple cartridge 112 includes inner walls 115 (FIG. 8). Each inner wall 115 defines a camming slot 115a that receives the corresponding camming portion 504 of the cam block 500. The camming portions 504 of the cam block 500 slides within the respective camming slots 115a of the staple cartridge 112. In this manner, the protrusions 502 of the cam block 500 are biased out of the respective slots 112d of the staple cartridge 112 by the spring 530 and guided by the camming portion 504 such that the protrusions 502 are substantially orthogonal to a buttress mounting surface 119 of the staple cartridge 112. However, when the tapered portion 502a (FIG. 7) of the protrusion 502 engages the proximal portion 600a (FIG. 9) of the loading assembly 600, the loading assembly 600 displaces the cam block 500 into the staple cartridge 112 such that the protrusions 502 of the cam block 500 are substantially flush with or beneath the buttress mounting surface 119, as will be described below.

Figure 9:
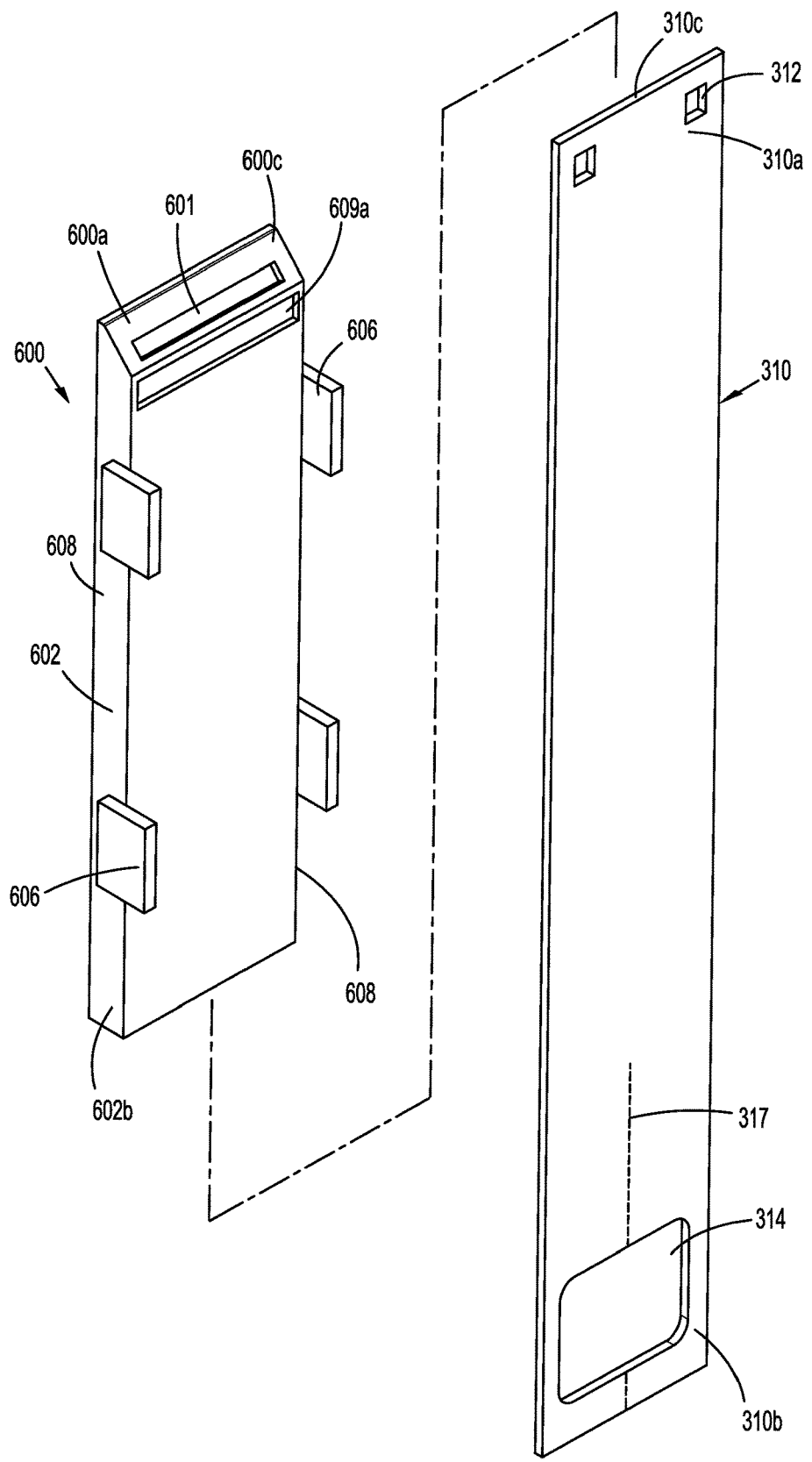
FIG. 9 is a perspective view of a buttress assembly for use with the surgical stapling device of FIG. 1, illustrating the buttress material separated from a loading assembly of the buttress assembly.
Figure 10:
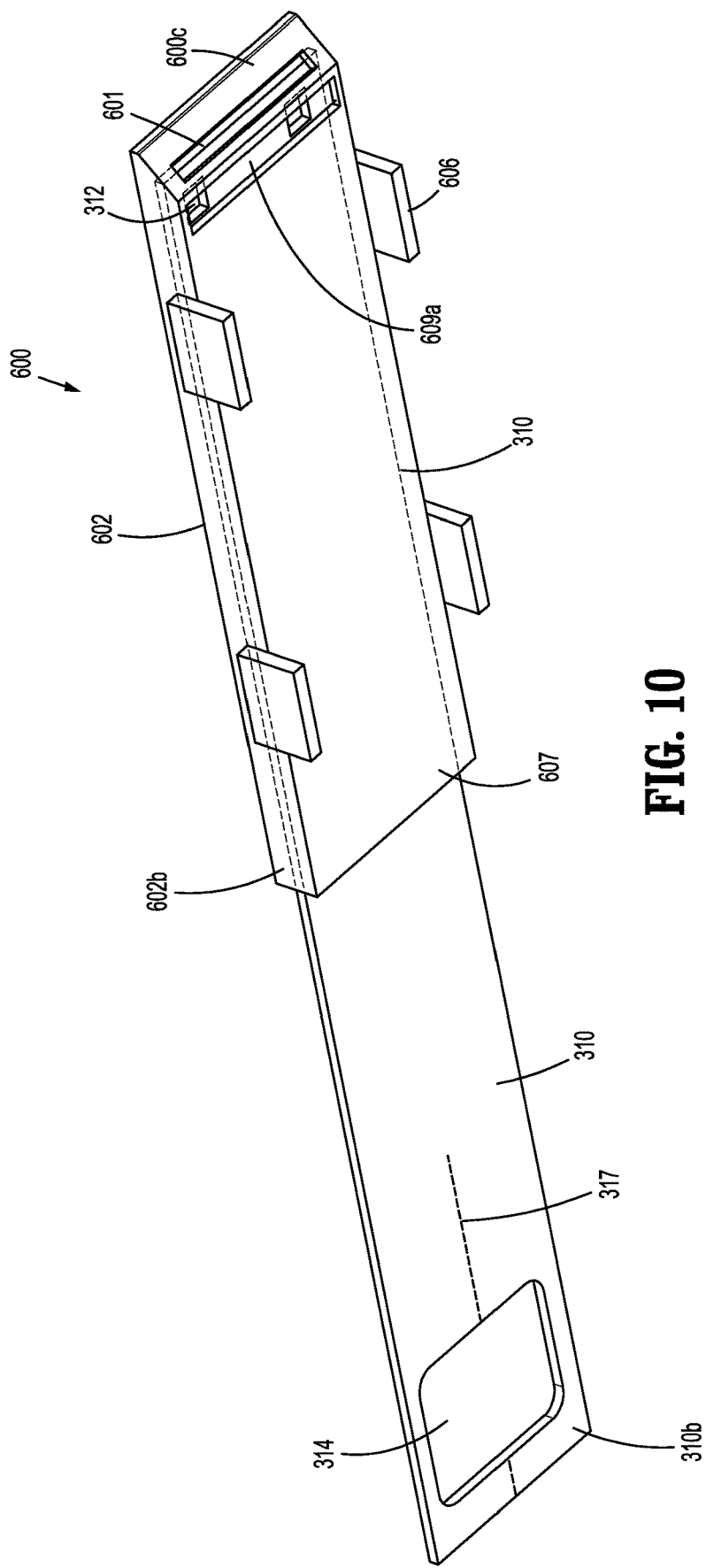
FIG. 10 is a perspective view of the buttress assembly of FIG. 9, illustrating the loading assembly mounted on the buttress material.
Figure 13:
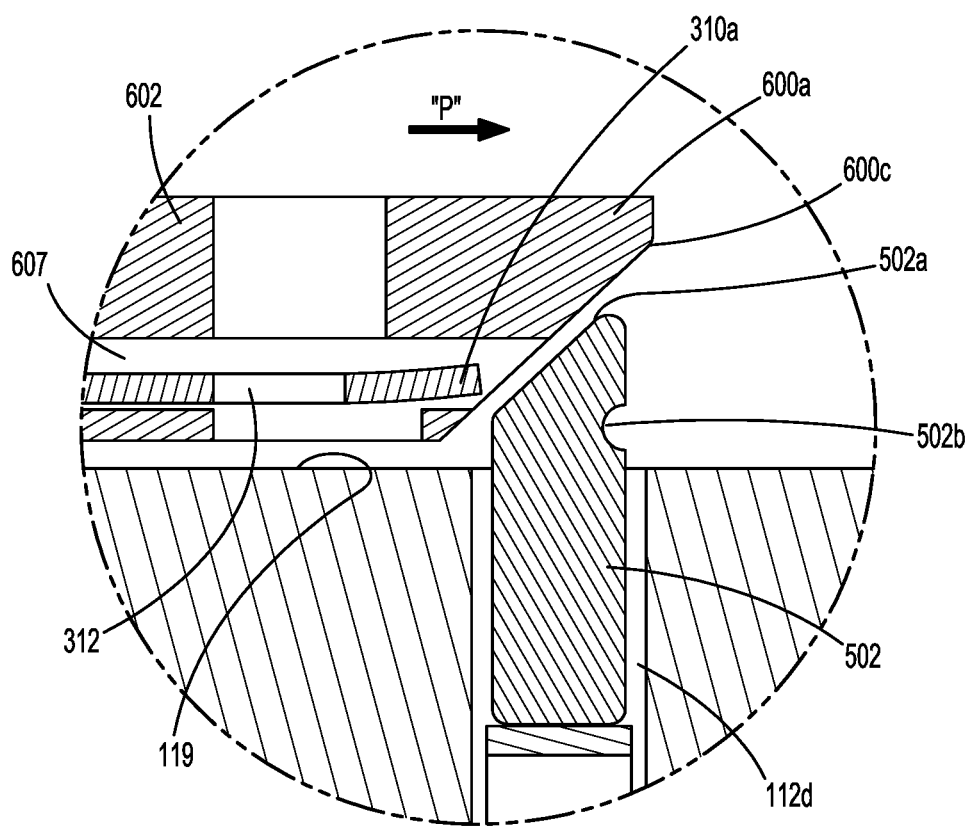
FIG. 13 a cross-sectional view of the staple cartridge and the buttress assembly of FIG. 12 taken along section line 13-13 of FIG. 12.

FIGS. 9 and 10 illustrate the loading assembly 600 that may be utilized in conjunction with the buttress material 310 to facilitate mounting of the buttress material 310 on the staple cartridge 112 (FIG. 6). In particular, the loading assembly 600 includes a housing 602 defining a chamber 607 (FIG. 13) configured to receive a portion of the buttress material 310 therein. The proximal portion 600a of the loading assembly 600 has a tapered portion 600c that defines an opening 601 to, e.g., visualize, placement of the buttress material 310 within the housing 602. In addition, the proximal portion 600a further defines a slot 609a dimensioned to receive the buttress material 310 therethrough. The slot 609a faces the buttress mounting surface 119 (FIG. 8) of the staple cartridge 112 when the loading assembly 600 is mounted on the staple cartridge 112. The housing 602 further includes a distal portion 602b defining a mouth 603 (FIG. 11) dimensioned to receive the buttress material 310 therethrough. The housing 602 includes a plurality of tabs 606 that are disposed on lateral sides 608 of the housing 602 to position the staple cartridge 112 within the tabs 606 and to facilitate axial displacement of the housing 602 along a length of the staple cartridge 112.

Figure 11:
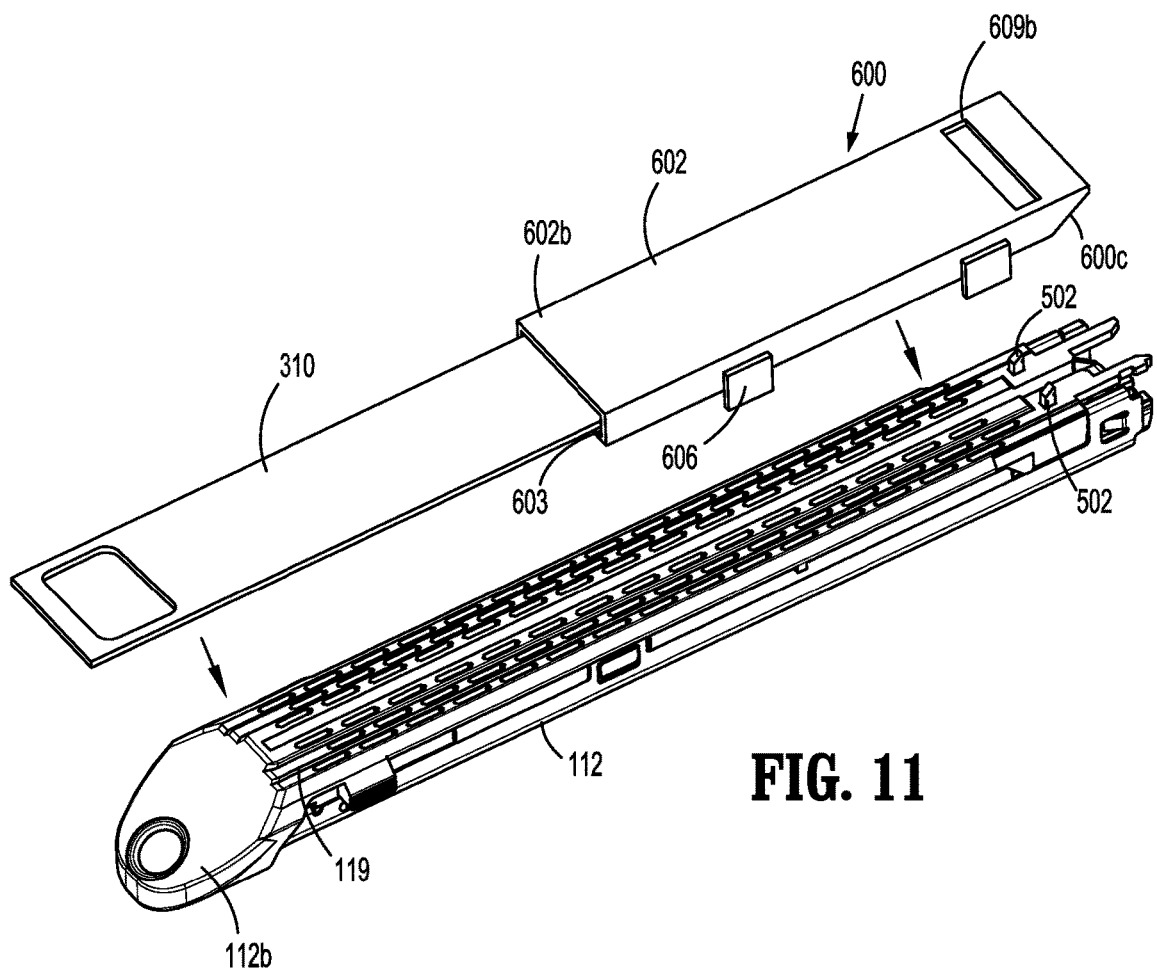
FIGS. 11 and 12 are perspective view of the staple cartridge of FIG. 6 and the buttress assembly of FIG. 10, illustrating mounting of the buttress assembly on the staple cartridge.
Figure 12:
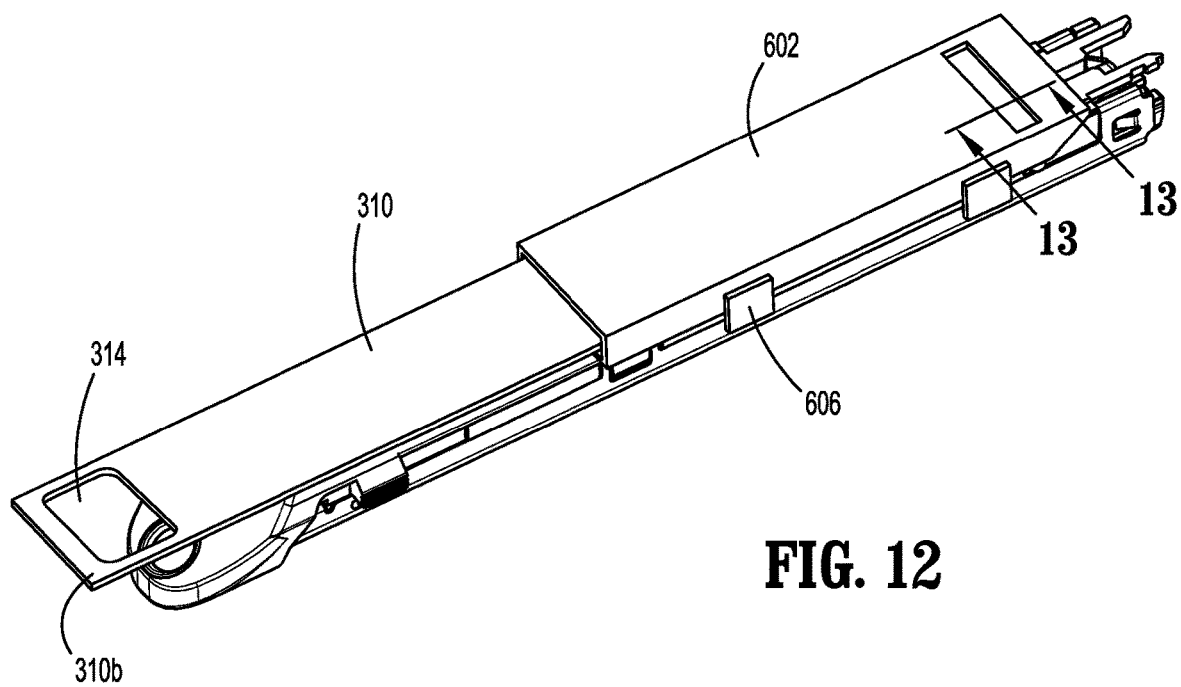
Figure 14:
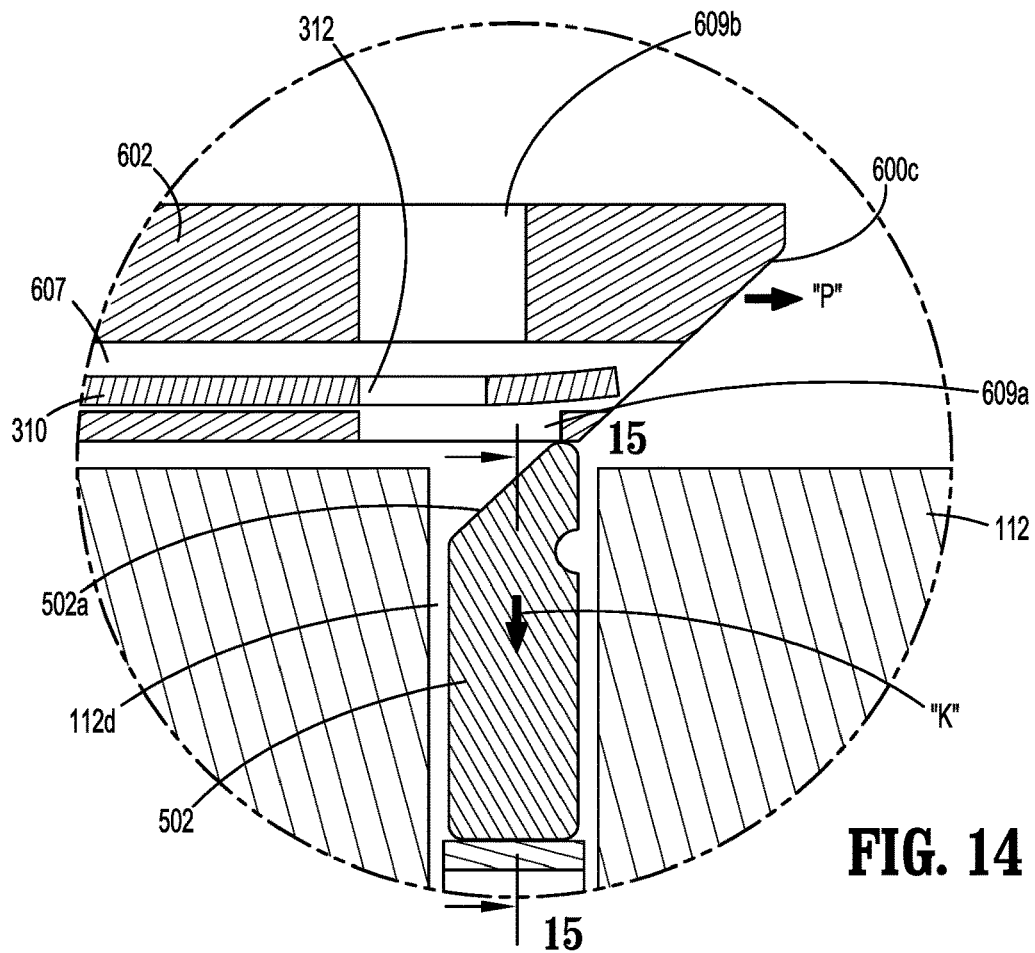
FIG. 14 a partial cross-sectional view of the staple cartridge and the buttress assembly of FIG. 12, illustrating mounting of the buttress assembly to the staple cartridge.
Figure 15:
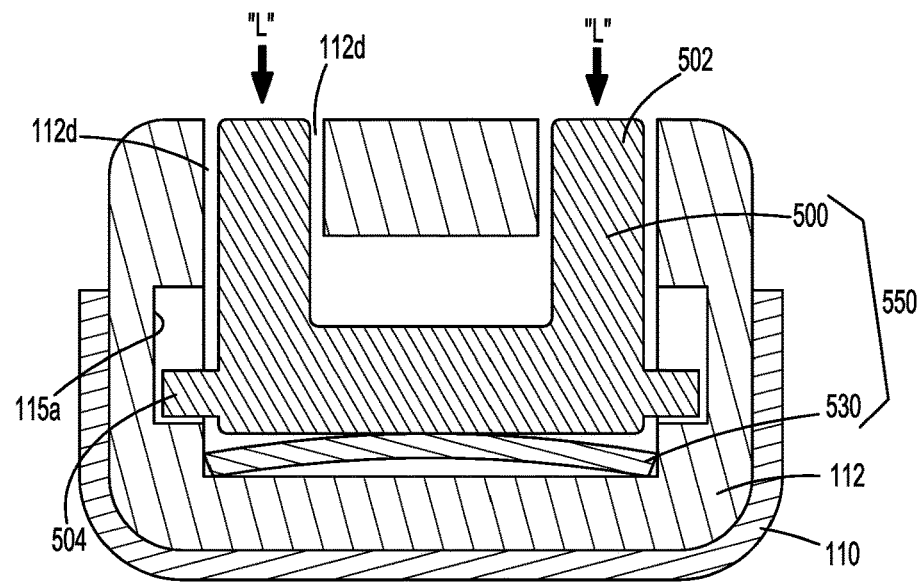
FIG. 15 is a cross-sectional view of the tool assembly of FIG. 3 taken along section line 15-15 of FIG. 14.
Figure 16:
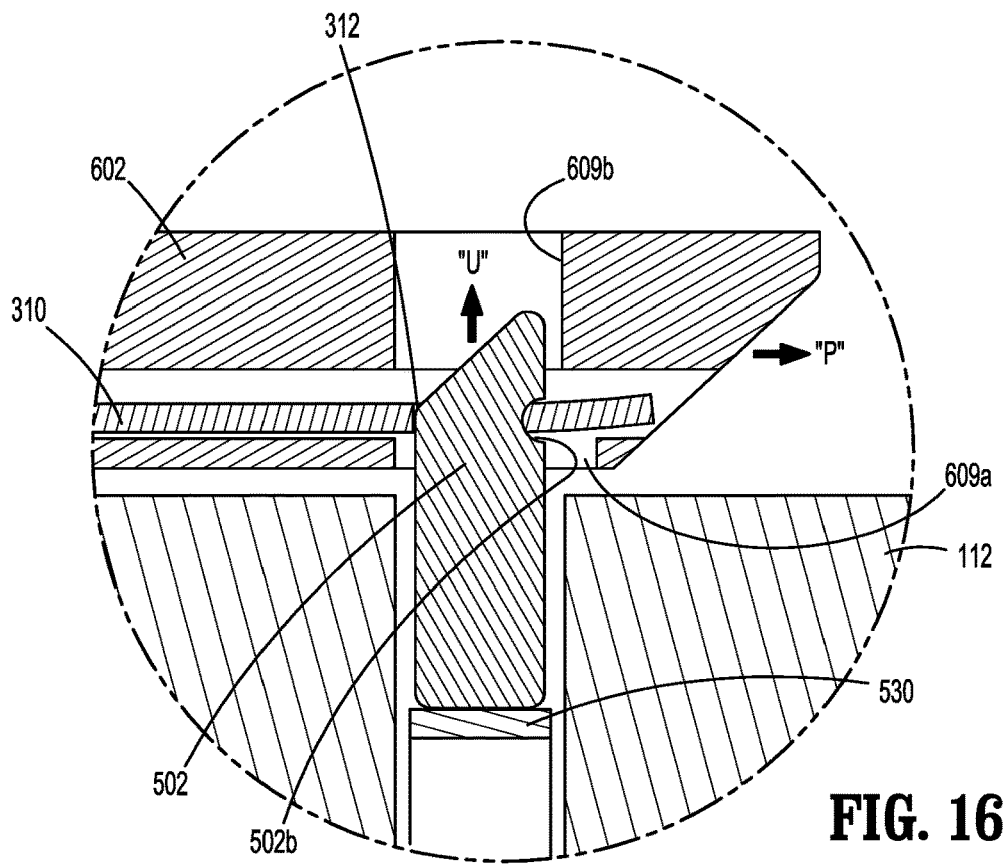
FIG. 16 is a partial cross-sectional view of the staple cartridge and the buttress assembly of FIG. 12, illustrating mounting of the buttress assembly to the staple cartridge.
Figure 17:
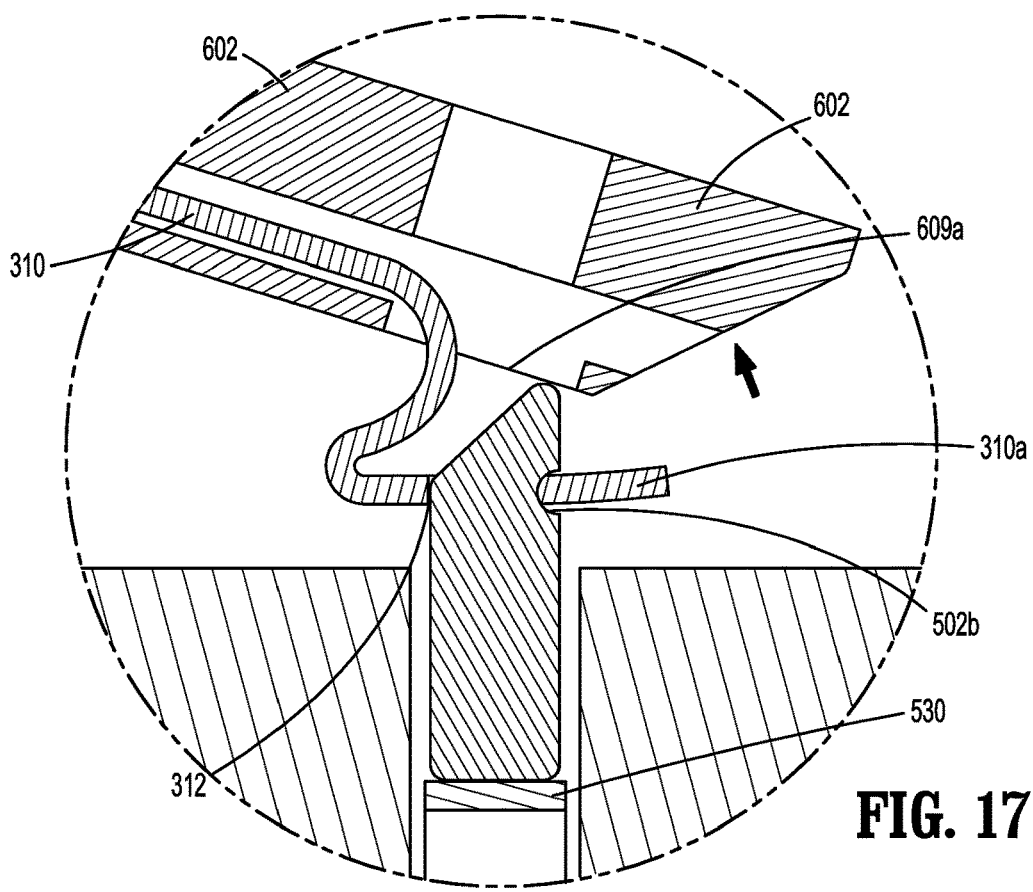
FIGS. 17 and 18 are partial cross-sectional views of the staple cartridge and the buttress assembly of FIG. 16, illustrating removal of the loading assembly from the buttress material.
Figure 18:
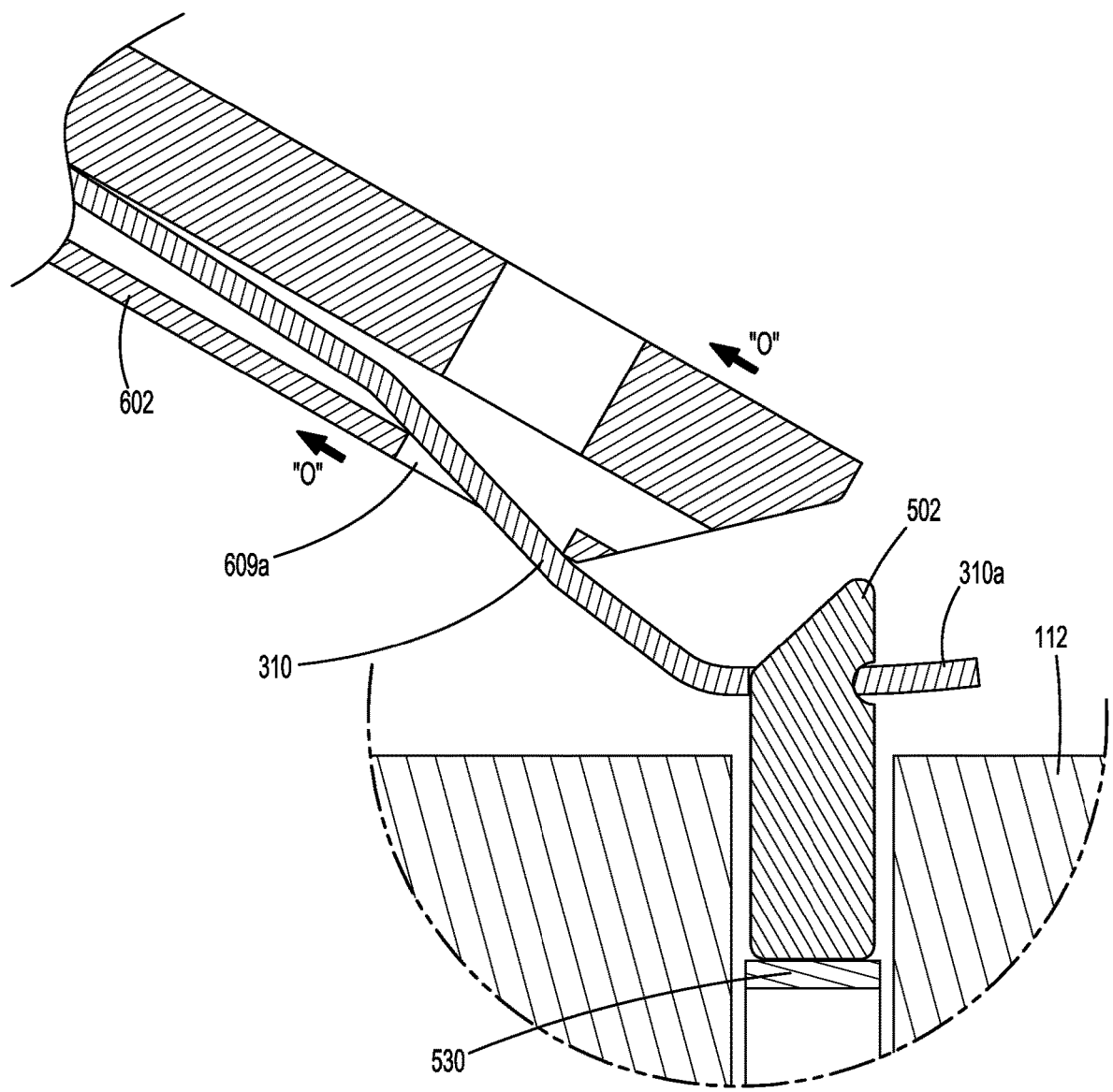

In use, the proximal portion 310a of the buttress material 310 is placed in the chamber 607 (FIG. 13) of the housing 602 of the loading assembly 600 through the mouth 603 (FIG. 11) of the housing 602 such that the bores 312 of the buttress material 310 are in registration with the slot 609a of the housing 602, as shown in FIG. 10. FIGS. 11 and 12 illustrate mounting of the buttress material 310 and the loading assembly 600 on the buttress mounting surface 119 such that the tapered portion 600c of the proximal portion 600a of the loading assembly 600 engages the tapered portion 502a (FIG. 7) of the protrusion 502 of the cam block 500 of the staple cartridge 512. As shown in FIGS. 14 and 15, the housing 602 along with the buttress material 310 is then displaced proximally in the direction of an arrow "P" such that the tapered portion 600c of the housing 602 displaces the protrusions 502 of the cam block 500 into the slot 112d of the staple cartridge 112. As the housing 602 is further displaced proximally in the direction of the arrow "P", the protrusions 502 of the cam block 500 extend through the bores 312 of the buttress material 310 in the direction of an arrow "U" via the slot 609a of the housing 602. The protrusions 502 are received in the slot 609b of the housing 602. In this manner, the buttress material 310 is detachably secured to protrusions 502 of the cam block 500, as shown in FIG. 16. The notch 502b of the protrusion 502 further enhances securement of the buttress material 310 to the protrusion 502. In an aspect, the protrusions 502 may engage the buttress material 310 via friction or interference fit. At this time, the housing 602 may be pulled distally as shown in FIGS. 17 and 18, which, in turn, causes the proximal portion 310a of the buttress material 310 and the protrusions 502 to pass through the slot 609a of the housing 602, as shown in FIG. 18. In this manner, the loading assembly 600 may be detached from the second jaw member 110 and the buttress material 310, while the proximal portion 310a of the buttress material 310 is releasably secured to the protrusions 502 of the cam block 500. At this time, the cavity 314 (FIG. 9) of the distal portion 310b of the buttress material 310 may be placed over the distal end portion 112b (FIG. 6) of the staple cartridge 112. The staple cartridge 112 having the buttress material 310 now mounted thereon may be supported on the second jaw 110 (FIG. 3) of the tool assembly 107 for stapling and severing of tissue.

It is further contemplated that the buttress material 310 may be made from any biocompatible natural or synthetic material. The material from which the buttress material 310 is formed may be bioabsorbable or non-bioabsorbable. It should be understood that any combination of natural, synthetic, bioabsorbable and non-bioabsorbable materials may be used to form the buttress material 310.

Some non-limiting examples of materials from which the buttress material 310 may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In aspects, natural biological polymers are used in forming the buttress material 310. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce the buttress material 310.

The buttress material 310 may be porous or non-porous, or combinations of porous and non-porous layers. Where the buttress material 310 is non-porous, the buttress material 310 may retard or inhibit tissue ingrowth from surrounding tissues thereby acting as an adhesion barrier and inhibiting the formation of unwanted scar tissue. Thus, in aspects, the buttress material 310 possesses anti-adhesion properties. Techniques for forming non-porous layers from such materials are within the purview of those skilled in the art and include, for example, casting, molding, and the like.

In aspects, the buttress material 310 is porous and possesses hemostatic properties. Where the buttress material 310 is porous, it has openings or pores over at least a portion of a surface thereof. Suitable materials for forming the porous layer include, but are not limited to foams (e.g., open or closed cell foams). In aspects, the pores may be in sufficient number and size so as to interconnect across the entire thickness of the porous layer. In other aspects, the pores do not interconnect across the entire thickness of the porous layer. In yet other aspects, the pores do not extend across the entire thickness of the porous layer, but rather are present at a portion of the surface thereof. In aspects, the openings or pores are located on a portion of the surface of the porous layer, with other portions of the porous layer having a non-porous texture. Those skilled in the art reading the disclosure will envision other pore distribution patterns and configurations for the porous layer.

Where the buttress material 310 is porous, the pores may be formed using any method suitable to forming a foam or sponge including, but not limited to the lyophilization or freeze-drying of a composition. Suitable techniques for making foams are within the purview of those skilled in the art. Porous buttress material 310 can be at least 0.2 cm thick, in aspects from about 0.3 to about 1.5 cm thick. Porous buttress material 310 can have a density of not more than about 75 mg/cm$^2$ and, in aspects below about 20 mg/cm$^2$. The size of the pores in the porous buttress material 310 can be from about 20 µm to about 300 µm, and in certain aspects from about 100 µm to about 200 µm.

The buttress material 310 may also include a reinforcement member. The reinforcement member may be associated with a porous or non-porous layer or may be positioned between a non-porous layer and a porous layer of the buttress material 310. Alternatively, the reinforcement member may be positioned entirely within one or more of the individual layers (e.g., embedded within the porous layer, the non-porous layer, or both) of the buttress material 310. It is also envisioned that the reinforcement member may be positioned at the surface of one of the layers making up the buttress material 310 and, in aspects, may be positioned at an exterior surface of the buttress material 310.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling, or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material 310. As another example, the monofilaments or multifilament braids may be oriented in a common direction within the buttress material 310. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped fibers may be from 0.1 mm to 100 mm in length, and in some aspects, 0.4 mm to 50 mm in length. In an aspect, the buttress material 310 has randomly oriented chopped fibers that have not been previously fused together and are embedded within in the buttress material 310.

It is envisioned that the reinforcement member may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In aspects, at least one bioactive agent may be combined with the buttress material 310 and/or any of the individual components (the porous layer, the non-porous layer and/or the reinforcement member) used to construct the buttress material 310. In aspects, the buttress material 310 can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively, a bioactive agent could be any agent which provides a therapeutic or prophylactic effect such as a compound that affects or participates in tissue growth, cell growth, or cell differentiation.

Examples of classes of bioactive agents which may be utilized in accordance with the disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to inhibit adhesions from forming between the buttress material 310 and the surrounding tissues opposite the target tissue. Some examples of these agents include, but are not limited to poly (vinyl pyrrolidone), carboxymethyl cellulose, hyaluronic acid, polyethylene oxide, poly vinyl alcohols and combinations thereof.

Suitable antimicrobial agents which may be included as a bioactive agent in the buttress material 310 of the disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the disclosure.

Other bioactive agents which may be included as a bioactive agent in the buttress material 310 in accordance with the disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Figure 19:
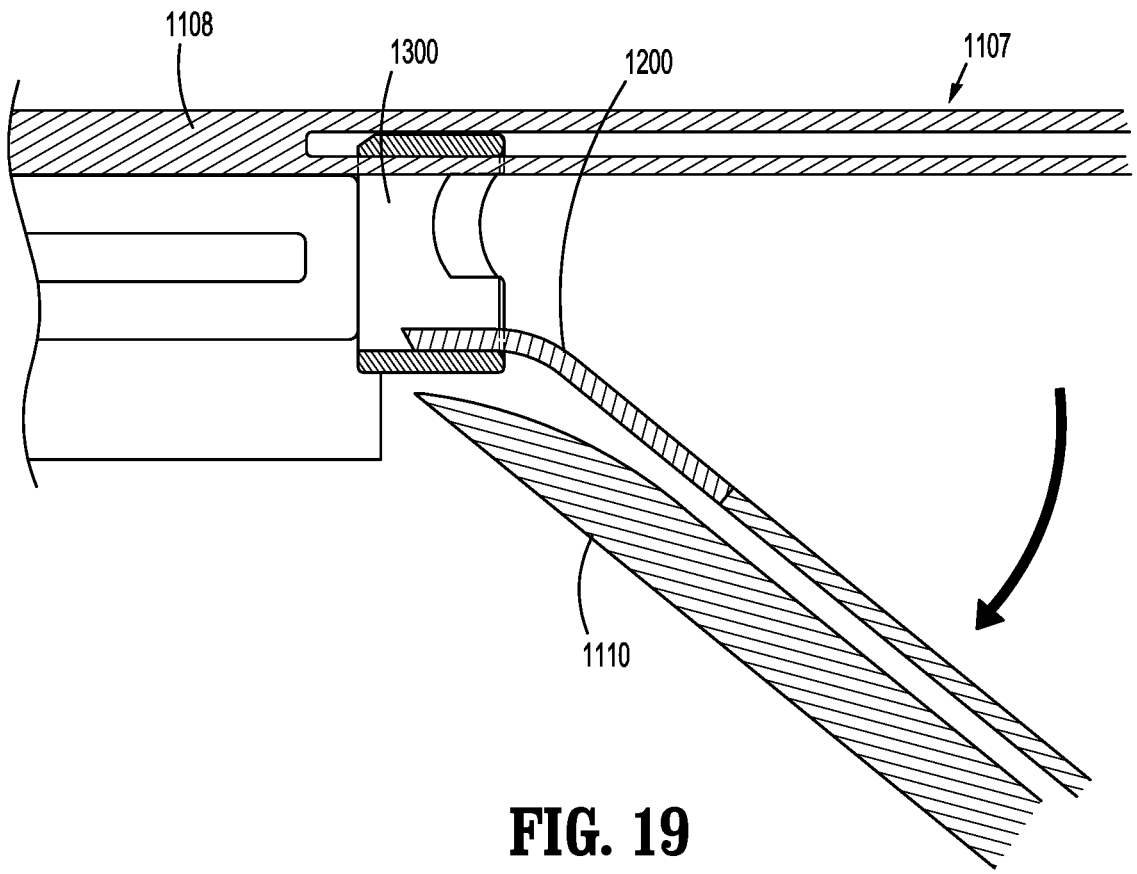
FIG. 19 is a partial cross-sectional view of a tool assembly in accordance with another aspect of the disclosure.
Figure 20:
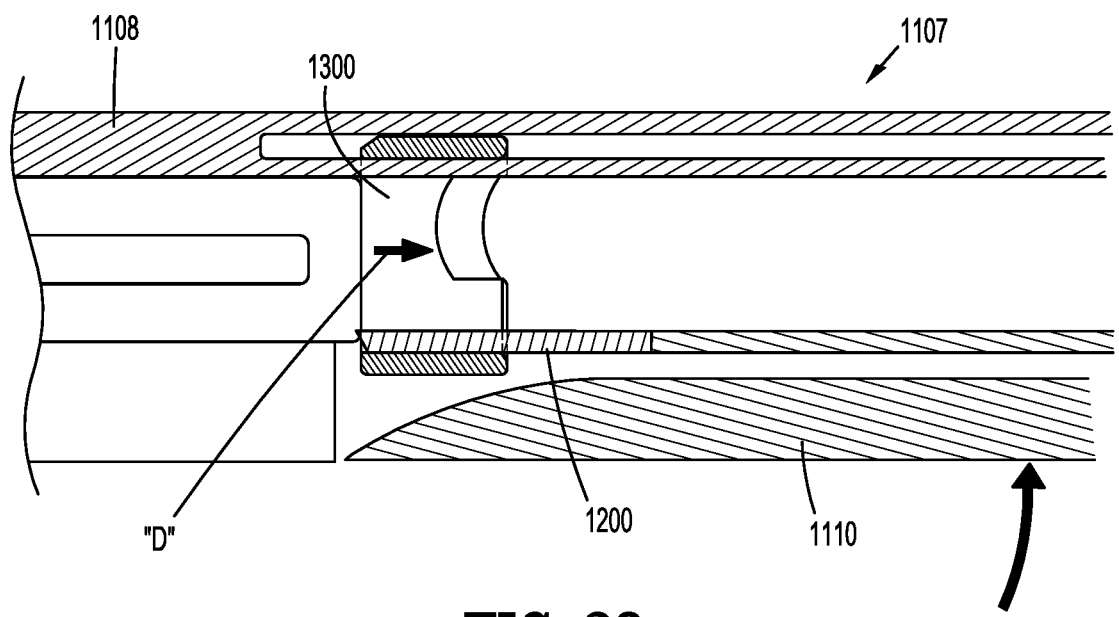
FIG. 20 is a partial cross-sectional view of the tool assembly of FIG. 19, illustrating clamping of jaw members of the tool assembly.

FIG. 19 illustrates a tool assembly 1107 in accordance with another aspect of the disclosure. The tool assembly 1107 includes a first jaw member 1108 and a second jaw member 1110 that is transitionable between an open configuration and a closed configuration in relation to the first jaw member 1108. Axial displacement of a clamping member 1300 transitions the second jaw member 1110 between the open and closed configurations. In particular, the second jaw member 1110 includes a spring 1200 that biases the second jaw member 1110 to the open configuration when the clamping member 1300 is in a proximal-most position. However, as the clamping member 1300 is advanced in the direction of an arrow "Y", the clamping force created by the clamping member 1300 overcomes the biasing force and transitions the second jaw member 1110 to the closed configuration, as shown in FIG. 20. In use, the clamping member 1300 is operatively coupled to the handle 202 such that when the button 26a (FIG. 1) is pressed, the clamping member 1300 is advanced distally. In an aspect, the spring 1200 may be disposed laterally of the clamping member 1300. In another aspect, the spring 1200 may include bifurcated arms to receive the clamping member 1300 between the bifurcated arms.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:
1. A surgical kit comprising:
   a surgical stapling device including:
      a tool assembly including first and second jaw members that are transitionable between open and closed configurations, the first jaw member supporting a staple cartridge that includes a retention assembly, the retention assembly including:
         a cam block including a pair of protrusions; and
         a spring biasing the cam block towards the second jaw member; and
      a buttress material including proximal and distal portions, the proximal portion defining bores laterally spaced apart and configured to receive the pair of protrusions of the cam block, the distal portion defining a cavity to be placed over a distal end portion of the staple cartridge; and
   a loading assembly including a housing defining a chamber configured to receive a portion of the buttress material, the housing including a proximal portion defining a slot configured to receive the buttress material therethrough and the pair of protrusions of the cam block.

2. The surgical kit according to claim 1, wherein the distal portion of the buttress material has a weakened portion extending axially from the cavity.

3. The surgical kit according to claim 1, wherein the housing of the loading assembly includes a pair of lateral tabs on lateral sides of the housing, the staple cartridge positioned within the pair of lateral tabs.

4. The surgical kit according to claim 1, wherein the proximal portion of the housing has a tapered surface.

5. The surgical kit according to claim 4, wherein the tapered surface of the proximal portion of the housing defines an opening.

6. The surgical kit according to claim 1, wherein the spring of the retention assembly is a leaf spring.

7. The surgical kit according to claim 1, wherein at least one protrusion of the pair of protrusions of the retention assembly has a tapered portion.

8. The surgical kit according to claim 1, wherein at least one protrusion of the pair of protrusions defines a notch positioned to receive a portion of the buttress material.

9. The surgical kit according to claim 1, wherein the staple cartridge includes an inner wall defining a camming slot, and the cam block includes a camming portion configured to slidably engage the camming slot of the inner wall.

10. The surgical kit according to claim 1, wherein the buttress material is formed of an elastic material and the buttress material is in tension when secured to the staple cartridge.

11. The surgical kit according to claim 1, wherein the pair of protrusions of the cam block is secured to the buttress material via interference or friction fit.

12. A buttress assembly for use with a surgical stapling device comprising:
   a buttress material including proximal and distal portions, the proximal portion defining bores laterally spaced apart, the distal portion defining a cavity; and
   a loading assembly including a housing defining a chamber to receive a portion of the buttress material, the housing including proximal and distal sections, the proximal section defining a slot configured to be in registration with the bores of the buttress material when the portion of the buttress material is received in the chamber of the loading assembly, the slot dimensioned to receive the buttress material therethrough.

13. The buttress assembly according to claim 12, wherein the housing has tabs on lateral sides thereof.

14. The buttress assembly according to claim 12, wherein the proximal section of the housing has a tapered surface.

15. The buttress assembly according to claim 14, wherein the tapered surface of the housing has an opening.

16. The buttress assembly according to claim 12, wherein the buttress material is bioabsorbable.

17. The buttress assembly according to claim 12, wherein the buttress material has perforations along a central axis of the buttress material.

18. The buttress assembly according to claim 12, wherein the cam block has a generally U-shaped profile.

19. A tool assembly of a surgical device comprising:
   a first jaw member;
   a second jaw member movable between open and closed configurations in relation to the first jaw member, the second jaw member including a spring to bias the second jaw member towards the open configuration, the spring being parallel to the second jaw member when the second jaw member is in the closed configuration; and
   a clamping member operatively coupled to the first and second jaw members such that axial displacement of the clamping member transitions the second jaw member between the open and closed configurations.

20. The tool assembly according to claim 19, wherein the spring is disposed laterally of the clamping member.

* * * * *